US007897161B2

(12) United States Patent
Yamada et al.

(10) Patent No.: US 7,897,161 B2
(45) Date of Patent: Mar. 1, 2011

(54) EXTERNAL MEDICINE FOR TREATING DERMATITIS

(75) Inventors: Hajime Yamada, Chiba-ken (JP); Akira Yamada, Chiba-ken (JP)

(73) Assignee: CAC Corporation (JP)

( * ) Notice: Subject to any disclaimer, the term of this patent is extended or adjusted under 35 U.S.C. 154(b) by 1081 days.

(21) Appl. No.: 10/516,657

(22) PCT Filed: Nov. 12, 2002

(86) PCT No.: PCT/JP02/11747

§ 371 (c)(1), (2), (4) Date: Dec. 1, 2004

(87) PCT Pub. No.: WO03/101460

PCT Pub. Date: Dec. 11, 2003

(65) Prior Publication Data

US 2005/0175640 A1 Aug. 11, 2005

(30) Foreign Application Priority Data

Jun. 3, 2002 (JP) ................................ 2002-161000

(51) Int. Cl.
*A61K 8/00* (2006.01)

(52) U.S. Cl. ................ 424/401; 514/53; 514/59; 514/23

(58) Field of Classification Search ........................ None
See application file for complete search history.

(56) References Cited

U.S. PATENT DOCUMENTS 3,574,854 A 4/1971 Bossard
3,777,597 A 12/1973 Herb
3,859,436 A 1/1975 Jacobi
5,547,997 A * 8/1996 Kludas .......................... 514/773
5,578,300 A * 11/1996 Schmidt et al. ............ 424/78.08
5,885,978 A 3/1999 Yamada et al.
5,980,916 A * 11/1999 Yvin et al. .................... 424/401
6,875,754 B1 * 4/2005 Griesbach et al. .............. 514/54
2003/0130248 A1 * 7/2003 Mozzone et al. ............. 514/179

FOREIGN PATENT DOCUMENTS

EP 0668072 A1 * 8/1995
EP 780129 * 6/1997
JP 9-157171 6/1997
JP 93 15987 12/1997
JP 10025240 * 1/1998
JP 11-180813 7/1999
JP 2002-060314 2/2002
JP 2002-114670 4/2002
WO WO 98/40082 9/1998

OTHER PUBLICATIONS

Supplemental European Search Report, dated Feb. 23, 2006, total 3 pages.

* cited by examiner

*Primary Examiner* — Lakshmi S Channavajjala

(74) *Attorney, Agent, or Firm* — Ostrolenk Faber LLP

(57) ABSTRACT

An external medicine for treating dermatitis wherein an adrenocortical steroid is included by a cyclodextrin; and 0.025 to 0.5% by weight of the adrenocortical steroid, 0.2 to 30% by weight of the cyclodextrin, and 0.5 to 55% by weight of dextran or pullulan are dissolved in an aqueous solution containing polysaccharide; and 0.5 to 55% by weight of xyloglucan, trehalose, laminaran, krestin, and pectin are blended. Grape sugar, mutan, lentinan, sodium chloride, and potassium chloride are comprised in the medicine. The medicine has a higher cure effect on atopic dermatitis and psoriasis vulgaris.

10 Claims, No Drawings

EXTERNAL MEDICINE FOR TREATING DERMATITIS

TECHNICAL FIELD

The present invention relates to external medicine for treating dermatitis wherein the medicine is especially effective against atopic dermatitis and seborrheic dermatitis, and which is very safe.

BACKGROUND ART

Conventionally, steroid drugs such as an adrenocortical hormone and the like which have a high antiinflammatory effect are mainly used for the medical treatment of dermatitis such as atopic dermatitis. As such a steroid drug of this type, they are many drugs which have been used wherein a vaseline, a methylcellulose, a surface active agent, a synthetic resin emulsion, a fine particles and/or the like are added to the steroid drug and they are creamed in accordance with the purpose of use. Moreover, there are liquid form steroid drugs which contain a surface active agent.

On the other hand, there are other external medicines having high safety which are aimed to have (1) sterilization and disinfection action on skin, (2) coating function, (3) moisturizing accelerating function by preventing evaporation of moisture of skin, and the like. To these types of the external medicines, an ingredient which use inorganic salt such as sodium chloride and the like (U.S. Pat. No. 3,574,854), an ingredient which uses natural sugar such as grape sugar and the like (U.S. Pat. No. 3,859,436), or an ingredient which uses plasma and the like (U.S. Pat. No. 3,777,597) are used as compounding ingredients of the external medicine.

Furthermore, an external medicine for treating dermatitis, which is effective for atopic dermatitis, seborrheic dermatitis, eczema, and the like and is very safe, has been invented by the inventor of the present invention. (Japanese Patent No. 2,920,611). This external medicine for treatment is a medicine such that adrenocortical steroid is included by a cyclodextrin to form clathrates, and polysaccharides which is dextran or pullulan is added thereto. This external medicine does not inhibit the physiological function of skin, and make it possible to obtain the synergistic effect of the adrenocortical steroid and natural healing energy with which the living body itself is equipped.

However, although the adrenocortical steroid has a high medicinal value such as the antiinflammatory effect and inhibition of multiplication of a fibroblast, it cannot provide good effect for some reason or other when it is used for the medical treatment of atopic dermatitis and the like. The reason is not clear at present as to the causes of the aforementioned not good effect. However, there is one opinion that such a not good effect is caused by the oil contained in the ointment or the oil used for providing the shape of cream, and the oil contained dissolves the horny layer of the skin and prevents reproduction of the healthy skin. Moreover, there are risks of side effects, such as an inhibition of functions of a pituitary gland and adrenal cortex, and functional disorder of the eye, other internal organs and the like, wherein these risks may be caused when a large amount of an adrenocortical steroid agent is used. In order to solve these problems, it is desired that the amount of the steroid which has been used for treatment be reduced while the high medicinal effect of the steroid as an antiinflammatory agent maintained.

Moreover, an external medicine which uses sodium chloride and the like and has high safety makes it possible to achieve the purposes of sterilizing and protecting skin such as softening skin, providing a sanitary condition to skin, and smoothing skin. However, an effect which is effective in the medical treatment of dermatitis such as atopic dermatitis is not observed by such a external medicine using sodium chloride and the like.

On the other hand, the aforementioned external medicine for treatment of the dermatitis, wherein the medicine was invented previously by the inventors of the present invention, can prevent an inhibition of the cell internal respiration, which is caused by disorder of the membrane of a mitochondria, and can prevent a lowering of production of ATP (adenosine triphosphate) which is a source of activity of the cell.

Furthermore, by the aforementioned external medicine, it is possible to maintain electrolyte balance and osmotic pressure balance, and to make the medicinal effect of an adrenocortical steroid act effectively. As a result of these features, the curing effects were widely observed from the external medicine on many conditions, such as atopic dermatitis, seborrheic dermatitis, psoriasis vulgaris, eczema, acne and the like. In these conditions that cured, the seborrheic dermatitis, eczema, acne, and the like were able to show effectiveness rates which showed an average of 96% or more. On the other hand, the atopic dermatitis showed effectiveness rate which was an average of only about 95%, and the psoriasis vulgaris showed effectiveness rate which was an average of only about 90%.

That is, when the aforementioned external medicine for treatment was used, the stable high effect was observed with respect to the seborrheic dermatitis, eczema, the acne and the like, but a variation of the effect was observed in atopic dermatitis, and an inferior result compared with other conditions was observed in psoriasis vulgaris.

The present invention aims to further improve the aforementioned external medicine for treating dermatitis in order to provide an external medicine for treating dermatitis, which has higher curing effect especially for atopic dermatitis and psoriasis vulgaris.

DISCLOSURE OF INVENTION

The present invention prepares an external medicines for treating dermatitis, wherein a cyclodextrin include an adrenocortical steroid is dissolved in an aqueous solution containing a polysaccharide; and 0.025 to 0.5% by weight of the adrenocortical steroid, 0.2 to 30% by weight of the cyclodextrin, and 0.5 to 55% by weight of a dextran or a pullulan are comprised. In this pharmaceutical, 0.5 to 55% by weight of each xyloglucan, trehalose, laminaran, krestin, and pectin are blended. At this time, after the adrenocortical steroid is dissolved at room temperature using a homo-mixer to include the adrenocortical steroid in the cyclodextrin, they are added in the aqueous solution while stirring the solution uniformly.

As other ingredients which are added to the aqueous solution, grape sugar, mutan, lentinan, sodium chloride, and potassium chloride are added into the aqueous solution. By such a solution, the similar environment as those obtained by intercellular substance liquid is made in a cell, and the cell can promote the tendency to perform normal activity. As a result, synergism between the natural curing energy with which the living body itself is provided and the adrenocortical steroid agent can be provided.

BEST MODE FOR CARRYING OUT THE INVENTION

The basic compounding of the present invention is that an adrenocortical steroid is dissolved in the aqueous solution containing a polysaccharide wherein the adrenocortical steroid is beforehand included by a cyclodextrin, in order to dissolve the adrenocortical steroid, which has hardness of dissolving in water, in an aqueous solution.

As an adrenocortical steroid, diflorasones, hydrocortisones, methyl predonisolones, dexamethasones, and betamethasones are mainly used. The content of the adrenocortical steroid is 0.025 to 5% by weight based on the entire contents. Moreover, the content of the cyclodextrin which contains the adrenocortical steroid is 0.2 to 40% by weight based on the entire contents.

Furthermore, each xyloglucan, laminaran, krestin, trehalose, and pectin is blended in an amount of 0.5 to 55% by weight.

Xyloglucan is a component sugar chain which exists universally in the wall (primary wall) of a plant cell which has elongated and hypertrophied. Plant species specificity is produced when galactose or fucosyl-galactose combines with a xylose residue. Lectin can combine with the galactose residue and the fucose residue respectively, but the function of these branch sugar chain is not solved. Growth of a plant cell is provided according to the water absorption phenomenon which is originating in the osmotic pressure which the cell has, and the suction force is produced by reduction of wall pressure which is caused by the slack of a cell wall. Although the slack of the cell wall is not yet solved, cell extension is always performed with solubilization and decomposition of xyloglucan, and xyloglucan is observed as one of the polysaccharides which manage the physiological activity of a cell.

Laminaran is one of the carbohydrates and is classified as a laminaran of β glucan. The laminaran is contained in mushrooms such as shiitake mushroom, and seaweeds such as kelp, and it has an effect which can increase immunity power. It is known that intake of the laminaran together with protein is preferable since the laminaran is difficult to absorbe when it is taken alone.

Krestin is used as immunological treatment remedy which reinforce expression of HLA class I antigen of a human cancer cell, and it is extracted from a coriolus versicolor mycelium. It is known that this krestin has an immunological medical treatment action in tumor diseases, such as stomach cancer, colon and rectal cancer, and small cell lung cancer.

Trehalose is one kind of sugar, and it is contained in mushrooms, seaweed, baker's yeast, and the like. Recently, the technology for making the trehalose artificially is established. Trehalose is used for providing a moisturizing effect, or be used as an alternative sweetener and the like. In the present invention, the trehalose is used as an ingredient of the external medicine of dermatitis in combination of other sugar.

Pectin is a natural polysaccharide which is known as a compositional ingredient of a vegetable cell wall, and it combines with ingredients such as cellulose to connect and unite cell membranes. The pectin is used as a gelling agent, thickener and stabilizer.

As a result of studying many polysaccharides to determine ingredients suitable for an external medicine, the inventors achieve the external medicine which is effective in atopic dermatitis and seborrheic dermatitis by combining the xyloglucan, laminaran, krestin, trehalose, and pectin.

Furthermore, a polysaccharide is added in the aqueous solution which dissolves an adrenocortical steroid. Dextran, pullulan and the like are used as the polysaccharide, and the amount thereof is 0.5 to 60% by weight based on the entire contents. In addition to the polysaccharide, grape sugar, mutan, lentinan, sodium chloride, calcium chloride, and potassium chloride can be added in the solution which dissolves an adrenocortical steroid.

EXAMPLES

Next, the examples of prescription and a pharmacological test are given below, and the external medicine of the present invention is explained concretely.

Prescription Example 1

| | |
|---|---|
| Dextran | 3 (g) |
| Grape Sugar | 5 |
| Maltose | 5 |
| Mannitol | 15 |
| Sodium Chloride | 0.2 |
| Betamethasone | 0.06 |
| Cyclodextrin | 15 |
| Xyloglucan | 2 |
| Trehalose | 3 |
| Laminaran | 2.5 |
| Krestin | 3 |
| Pectin | 1.24 |
| Purified water | 45 |
| The entire content is | 100.0 g |

Aforementioned example of prescription was prepared as follows. At first, 10% solution of cyclodextrin was made by using purified water which was some part of purified water which had been prepared for this prescription. Then, betamethasone was added to the solution while conducting stirring. Xyloglucan, trehalose, laminaran, krestin, and pectin were further added to the solution with the remaining purified water and salts.

Next, the effect of the prescription example 1 is shown below.

TABLE 1

| Morbidity | Object number | Effectiveness | Effective rate | Comparison with a conventional prescription |
|---|---|---|---|---|
| Atopic dermatitis (1) | 50 | 98 | 98 | +2 |
| Atopic dermatitis (2) | 24 | 46 | 96 | +1 |
| Atopic dermatitis (3) | 56 | 110 | 98 | +6 |
| Atopic dermatitis (4) | 25 | 49 | 98 | 0 |
| Seborrheic dermatitis (1) | 43 | 80 | 93 | −3 |
| Seborrheic dermatitis (2) | 78 | 149 | 96 | −3 |
| Seborrheic dermatitis (3) | 10 | 18 | 90 | −5 |
| Psoriasis vulgaris | 10 | 19 | 95 | +5 |
| Eczema | 15 | 28 | 93 | −3 |
| Acne | 50 | 96 | 96 | −3 |

Table 1 shows the results of the pharmacological test of the prescription example 1. From the results, the effective rate of the atopic dermatitis, which is the most noted dermatitis in the present invention, is 96 to 98% and an average thereof is 97.5%. That is, it turns out that the medicine has high effective rate without variation thereof.

Furthermore, the quite high cure effect is observed in the psoriasis vulgaris such that the effective rate is 95%, although the rate does not reach the effective rate of atopic dermatitis. Moreover, the point which should be mentioned especially is that no side effects have been observed among the 300 cases.

This feature is also observed in the previous external medicine by the inventors, and the safety of the improved external medicine of the present invention was also verified by the evaluation.

Effectiveness was calculated by the following formula after obtaining total values of each object. The total values were obtained such that a result that did not show any change by use of the external medicine of the present invention was set as the zero point, a result that showed a change which is changed to be cured by use of the external medicine was made into one point, and a result wherein the effect was observed by the use of the external medicine was made into two points.

$$\text{Effective rate} = \frac{\text{Totaled value}}{\text{Object number} \times 2} \times 100 \quad \text{Formula 1}$$

These results of the pharmacological tests of the atopic dermatitis were carried out at each clinic in Nagareyama, Sendai, Omiya, and Kichijoji. The resulting data of the pharmacological test of other dermatitis were carried out at the Nagareyama clinic.

As shown in the results of the pharmacological test of the prescription example 1, 90% or more of curative improvement was observed in all effective rates, and there are people wherein the external medicine of the present invention act early and they no longer need the external medicine after about the seventh day to thirtieth day have passed. Furthermore, by applying a solution containing a polysaccharide but not containing an adrenocortical steroid (Japanese Patent No. 1,597,430) to the objects, the dermatitis was cured completely. Moreover, moisturizing effect to skin was evaluated in three levels "good", "normal" and "bad" in the experiment, and the results are shown below.

TABLE 2

| | Good | Normal | Bad |
|---|---|---|---|
| Number (person) | 356 | 14 | 0 |
| Ratio (%) | 96.2 | 3.8 | 0.0 |

As shown in the table 2, there is no person who evaluate the prescription example 1 as bad, and 96% or more people evaluate that the sensation is good when it is used.

Prescription Example 2

| | |
|---|---|
| Dextran | 10 (g) |
| Grape Sugar | 5 |
| Maltose | 10 |
| Mannitol | 5 |
| Sodium Chloride | 0.1 |
| Potassium Chloride | 0.2 |
| Sodium Betamethasonephosphate | 0.12 |
| Cyclodextrin | 10 |
| Xyloglucan | 2 |
| Trehalose | 8 |
| Laminaran | 6 |
| Krestin | 4 |
| Pectin | 12 |
| Purified water | 27.58 |
| The entire content is | 100.0 g |

Prescription Example 3

| | |
|---|---|
| Pullulan | 10 (g) |
| Betaine | 15 |
| Maltose | 10 |
| Sodium Chloride | 0.1 |
| Dexamethasone | 0.06 |
| Cyclodextrin | 15 |
| Xyloglucan | 6 |
| Trehalose | 3 |
| Laminaran | 2 |
| Krestin | 6 |
| Pectin | 3 |
| Purified water | 29.84 |
| The entire content is | 100.0 g |

Prescription Example 4

| | |
|---|---|
| Dextran | 5 (g) |
| Betaine | 20 |
| Maltose | 5 |
| Sodium Chloride | 0.1 |
| Sodium Betamethasonephosphate | 0.05 |
| Cyclodextrin | 6 |
| Xyloglucan | 2 |
| Trehalose | 5 |
| Laminaran | 7 |
| Krestin | 2 |
| Pectin | 8 |
| Purified water | 39.75 |
| The entire content is | 100.0 g |

Prescription Example 5

| | |
|---|---|
| Dextran | 10 (g) |
| Hydroxyethyl Cellulose | 2 |
| Betaine | 10 |
| Mannitol | 10 |
| Sodium Chloride | 0.1 |
| Calcium Chloride | 0.1 |
| Sodium Betamethasonephosphate | 0.1 |
| Cyclodextrin | 10 |
| Xyloglucan | 10 |
| Trehalose | 7 |
| Laminaran | 10 |
| Krestins | 2 |
| Pectin | 8 |
| Purified water | 20.7 |
| The entire content is | 100.0 g |

Prescription Example 6

| | |
|---|---|
| Pullulan | 10 (g) |
| Hydroxyethyl Cellulose | 6 |
| Betaine | 10 |
| Mannitol | 5 |
| Calcium Chloride | 0.1 |

-continued

| | |
|---|---|
| Sodium Chloride | 0.1 |
| Dextrin | 7 |
| Dexamethasone | 0.05 |
| Cyclodextrin | 5 |
| Xyloglucan | 6 |
| Trehalose | 9 |
| Laminaran | 6 |
| Krestin | 9 |
| Pectin | 8.5 |
| Purified water | 18.25 |
| The entire content is | 100.0 g |

It was found that the effects of the aforementioned prescription examples 2 to 6 followed the effect of the prescription example 1. The prescriptions can be suitably selected according to the condition of each dermatitis.

Next, comparison explanation is given about the conventional prescription and its medical value.

Prescription Example 7

Conventional Prescription

| | |
|---|---|
| Dextran | 10 (g) |
| Grape sugar | 10 |
| Maltose | 5 |
| Mannitol | 15 |
| Sodium chloride | 0.2 |
| Betamethasone | 0.06 |
| Cyclodextrin | 15 |
| Purified water | 44.74 |
| The entire content is | 100.0 g |

TABLE 3

| Morbidity | Object number | Effectiveness | Effective rate |
|---|---|---|---|
| Atopic dermatitis (1) | 25 | 48 | 96 |
| Atopic dermatitis (2) | 10 | 19 | 95 |
| Atopic dermatitis (3) | 25 | 46 | 92 |
| Atopic dermatitis (4) | 25 | 49 | 98 |
| Seborrheic dermatitis (1) | 25 | 48 | 96 |
| Seborrheic dermatitis (2) | 100 | 198 | 99 |
| Seborrheic dermatitis (3) | 10 | 19 | 95 |
| Psoriasis vulgaris | 5 | 9 | 90 |
| Eczema | 25 | 48 | 96 |
| Acne | 50 | 99 | 99 |

Table 3 shows the results of the pharmacological test of the prescription example 7 (the conventional prescription). (The calculation method of effectiveness and the clinic where the pharmacological test was conducted were the same as those of Table 1). As is apparent from the results, the effective rate of atopic dermatitis is only about 95%, and the effective rate of psoriasis vulgaris about an average of 90%, although the conventional prescription provide an average of 96% or more of effective rate with respect to the seborrheic dermatitis, eczema, acne and the like.

On the other hand, it is clear from the prescription example 1 that the cure effect is increased with respect to atopic dermatitis and a psoriasis vulgaris especially, by adding xyloglucan, trehalose, laminaran, krestin, and pectin.

INDUSTRIAL APPLICABILITY

An external medicine for treating dermatitis of the present invention is such that a cyclodextrin includes an adrenocortical steroid, and it is dissolved in an aqueous solution containing a polysaccharide, and 0.025 to 0.5% by weight of the adrenocortical steroid, 0.2 to 30% by weight of the cyclodextrin, and 0.5 to 55% by weight of a dextran or a pullulan is comprised. Furthermore, by including 0.5 to 55% of the weight of each xyloglucan, trehalose, laminaran, krestin and pectin in the external medicine, the excellent and stabilized cure effect is achieved even in the atopic dermatitis wherein the variation of an effect have been observed when the previous external medicine is used.

Moreover, even in the psoriasis vulgaris, which showed inferior cure effect compared with other dermatitises when the previous external medicine for treatment was used, the effective rate was able to be raised to the levels of other dermatitis by the present invention.

In this way, according to the present invention, it become possible to greatly raise an effective rate as compared with previous external medicines. Particularly, the external medicine of the present invention is very effective in diseases which have been difficult to cure such as atopic dermatitis, seborrheic dermatitis and the like. From viewpoints such as high cure rate and high safety such as extremely low side effects, the external medicine of the present invention can be used as a medicine which can supersede the conventional external medicine. The external medicine of the present invention can be expected to be used for a large number of patients and the like all over the world who have suffered from intractable dermatitis. The significance of the present invention is great, and it can greatly contribute to human beings.

The invention claimed is:

1. An external medicine for treating atopic dermatitis and psoriasis vulgaris wherein the external medicine is an aqueous solution comprising:

0.025 to 0.5% by weight of adrenocortical steroid, 0.2 to 30% by weight of cyclodextrin, 0.5 to 55% by weight of a dextran or pullulan; and 0.5 to 55% by weight of each xyloglucan, trehalose, laminaran, krestin, and pectin;

and wherein the medicine then further comprises at least one selected from the group consisting of grape sugar, mutan, lentinan, sodium chloride, and potassium chloride.

2. The external medicine for treating atopic dermatitis and psoriasis vulgaris according to claim 1, wherein the aqueous solution comprises said grape sugar and said sodium chloride.

3. The external medicine for treating atopic dermatitis and psoriasis vulgaris according to claim 1, wherein the adrenocortical steroid is included in the cyclodextrin.

4. A method of treating dermatitis with an external medicine, wherein the external medicine is an aqueous solution comprising:

0.025 to 0.5% by weight of adrenocortical steroid;

0.2 to 30% by weight of cyclodextrin;

0.5 to 55% by weight of dextran or pullulan; and 0.5 to 55% by weight of each of xyloglucan, trehalose, laminaran, krestin and pectin, and further comprising at least one selected from the group consisting of grape sugar, mutan, lentinan, sodium chloride and potassium chloride.

5. The treatment method according to claim 4, wherein the dermatitis is selected from the group consisting of atopic dermatitis, seborrheic dermatitis, psoriasis vulgaris, eczema and acne.

6. The treatment method according to claim 4, wherein the dermatitis is selected from the group consisting of atopic dermatitis and psorasis vulgaris.

7. The treatment method according to claim 4, wherein the aqueous solution further comprises at least said grape sugar and said sodium chloride.

8. The treatment method according to claim 4, wherein the adrenocortical steroid is included in the cyclodextrin.

9. The external medicine for treating atopic dermatitis and psoriasis vulgaris according to claim 1, wherein the medicine does not contain an oil.

10. The treatment method according to claim 4, wherein the medicine does not contain an oil.

* * * * *